United States Patent
Wick

(10) Patent No.: US 10,149,831 B1
(45) Date of Patent: *Dec. 11, 2018

(54) PHARMACEUTICAL COMPOSITION FOR TREATING BACTERIAL AND VIRAL INFECTIONS

(71) Applicant: Edward Wick, Sussex, WI (US)

(72) Inventor: Edward Wick, Sussex, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/893,199

(22) Filed: Feb. 9, 2018

Related U.S. Application Data

(63) Continuation-in-part of application No. 15/788,114, filed on Oct. 19, 2017, now Pat. No. 9,943,503.

(51) Int. Cl.

| | |
|---|---|
| *A61K 31/375* | (2006.01) |
| *A61K 31/59* | (2006.01) |
| *A61K 33/30* | (2006.01) |
| *A61K 31/07* | (2006.01) |
| *A61K 31/593* | (2006.01) |
| *A61P 31/04* | (2006.01) |
| *A61K 36/8962* | (2006.01) |
| *A61K 36/28* | (2006.01) |
| *A61K 9/20* | (2006.01) |
| *A61P 31/16* | (2006.01) |
| *A61K 31/4415* | (2006.01) |

(52) U.S. Cl.
CPC .............. *A61K 31/375* (2013.01); *A61K 9/20* (2013.01); *A61K 31/07* (2013.01); *A61K 31/4415* (2013.01); *A61K 31/593* (2013.01); *A61K 33/30* (2013.01); *A61K 36/28* (2013.01); *A61K 36/8962* (2013.01); *A61P 31/04* (2018.01); *A61P 31/16* (2018.01)

(58) Field of Classification Search
CPC ...... A61K 31/59; A61K 31/31; A61K 31/601; A61K 31/375
USPC ................ 514/167, 168, 474, 641, 725, 754
See application file for complete search history.

(56) References Cited

U.S. PATENT DOCUMENTS 9,943,503 B1 * 4/2018 Wick ................... A61K 31/375

OTHER PUBLICATIONS

Phillip, John,Natural News.Com Oct.13, 2012 B vitamin bolster immune response to tight infection and chronic disease.
Mayo Clinic Free E-Newsletter for dosing of vitamin B6.
Micronutrient Information Center, Linus Pauling Institute, Oregon State University, Corvallis, or, May 2014, for "Vitamin B6".

* cited by examiner

*Primary Examiner* — Raymond J Henley, III

(57) ABSTRACT

The present invention relates to a pharmaceutical; composition comprising an effective amount of vitamin C, zinc, vitamin A, vitamin D3, vitamin B6, garlic and Echinacea to treat bacterial and/or viral infections, and a method for treating bacterial and/or viral infections by orally administering the composition to a patient effective to reduce symptoms of bacterial and/or viral infections such a cold and influenza.

8 Claims, No Drawings

PHARMACEUTICAL COMPOSITION FOR TREATING BACTERIAL AND VIRAL INFECTIONS

FIELD OF INVENTION

The present invention relates generally to a pharmaceutical composition and its use. More specifically, the present invention is a pharmaceutical composition comprising an effective amount of vitamin C, zinc, vitamin A, vitamin D3, vitamin B6, garlic and Echinacea, to treat bacterial or viral infection, and a method for treating bacterial or viral infection by orally administrating the composition to a patient effective to reduce the symptoms of bacterial and/or viral infections such as cold or influenza.

BACKGROUND OF INVENTION

To treat bacterial infections a variety of antibiotics drugs are available. However, the over-prescription of antibiotics over the past half century give rise to antibiotic resistant strains of bacteria such as superbugs (1). More than 400 kinds of superbugs are known to cause human diseases. These diseases include, for example the common cold, influenza, cold sores (Herpes type 1), genital herpes (Type 2), norovirus, mononucleosis, shingles, hepatitis, dengue, West Nile fever, severe acute respiratory syndrome (SARS), Hantavirus, Ebola, and acquired immunodeficiency syndrome (AIDS), especially in cases of the common cold and influenza, rapid mutations make it difficult for the body immune system to identify and react to the invading viruses quickly (1). For viral infections in general, and upper respiratory viral infections in particular, effective drugs to hinder reproduction of the infectious agents are much less available. Prescription of anti-flu drugs currently available may reduce complications such as pneumonia, and often viruses are resistant to drugs. As an alternative to conventional pharmaceuticals for treating bacterial or viral infection, interest has grown in the use of certain food supplements for the enhancing or stimulating the immune system in the human body (2). One object of the present invention is to use and alternative composition to enhance or stimulate the immune system of the human body, thus to aid the body's ability to self-repair.

Wellness can be achieved with the behavioral and lifestyle modifications utilizing multimodal approaches. For example, with proper diet, especially vegetables, exercise, and botanical alternatives, this approach strives to improve the physical and emotional wellness of patients. The present inventor has identified certain alternatives. The inclusion of prevention and wellness management by physicians as a standard of patient care will decrease in medical errors and will contribute significantly in lowering the cost of health care.

It is therefore an aim of the present invention to provide and alternative composition for treating bacterial or viral infection in a patient, the alternative composition comprising an effective amount of vitamin C, zinc, vitamin A, vitamin D3, vitamin B6, garlic, and Echinacea; and a method for treating bacterial or viral infection in a patient effective to reduce the symptoms of bacterial and/or viral infections such as colds and influenza.

DETAIL DESCRIPTION OF THE INVENTION

The present invention is a oral composition comprising an effective amount of vitamin C, zinc, vitamin A, vitamin D3, vitamin B6, garlic, and Echinacea that is able to treat bacterial or viral infection in a patient. The oral composition is utilized by either adults or children. The oral composition incorporates active ingredients which function cooperatively to enhance or stimulate the immune system of the human body in order to treat bacterial or viral infection.

Vitamin C (ascorbic acid), is a water-soluble vitamin found in fruit and vegetables, such as citrus fruit (3). It is necessary for the iron absorption, wound healing and collagen formation. Vitamin C is also recognized as being important for the successful productions of neurotransmitters and improvement of glucose metabolism, its deficiency results in neurological disease of scurvy. Vitamin C, which is associated with immune strengthening, is derived from its ability to enhance the function of the immune system, including antimicrobial and NK cell activities, macrophages, lymphocyte proliferation, chemotaxis, and delayed-type hypersensitivity (3). The recommended daily intake by the US food and Nutrition Board of the Institute of Medicine for men more than 18 years old is 90 mg of vitamin C daily; for women more than 18 years old, it is 75 mg daily (4). For treating the common cold, 200 mg to 3 g have been taken by mouth daily for three to five days or longer (4).

Zinc salts have been found to inhibit rhinovirus replication in vitro at concentrations of <0.1 mmole/L, possibly by interfering with rhinovirus protein cleavage (3). It also has been suggested that zinc salts may protect plasma membranes against lysis by cytotoxic agents such as microbial toxins and complement. The proposed protective mechanism is either via immunomodulation or via the binding of zinc ions to rhinovirus surface canyons, thus inhibiting viral interactions with intercellular adhesions molecule-1 (ICAM-1), the site of rhinovirus binding to cells. Because ICAM-1 is also the binding site for leukocyte function associated antigen-1 (LEA-1), the block of LFA-1/ICAM-1 binding has been postulated to possibly suppress inflammation. Several randomized, controlled clinical studies showed a beneficial effect of using zinc for treating the common cold, particularly when zinc is started within the first 24 hours of onset of symptoms (3). The current recommended dietary allowance for zinc taken by mouth is: 11 mg for males 19 years and older; and 8 mg for females 19 years and older (5). For the common cold, doses have ranged from 4.5-24 mg of inc (gluconate or acetate) in the form of lozenges taken by mouth every 1-3 hours for 3-14 days or until symptoms resolved.

Vitamin A, use as a dietary supplement, for adults and teenagers: oral dosage form (capsules or chewable tablets) has 6-15 mg of beta-carotene (the equivalent of 10.000-25000 units of vitamin A activity) per day (6). For children, the oral dosage is 3 to 6 mg of beta carotene (the equivalent of 5,000-10,000 units of vitamin A activity) per day.

Vitamin D is usually in strengths from 50 to 100 international units (IU), it can be found as a soft gel, capsules, tablets and liquids (7). The 2010 recommended daily allowance (RDA) is 600 IU for those 1-71 years of age and 800 IU for those over 71 years of age. For immune function, the following doses have been taken by mouth: 40 IU of vitamin D3 daily for 20 years to 100,000 IU of vitamin D3 bimonthly for 12 months, or 10,000 IU daily. For the treatment of respiratory infections, 2000 IU per kilogram body weight has been taken by mouth daily for three days. For viral infections, 800 IU of vitamin D has been taken by mouth daily for two years, followed by 2000 IU of vitamin D daily for 12 months. For viral infection, 60,000 IU has been taken by mouth weekly for six weeks.

Vitamin B6 refers to a group of chemically similar compounds which can be interconverted in biological systems. Vitamin B6 is part of the vitamin B group of essential nutrients. Its active form, pyridoxal 5-phosphate serves as a coenzyme in some 100 enzyme reactions in amino acid, glucose and lipid metabolism (10). Vitamin B6 is widely distributed in foods in both its free and bound forms. Cooking, storage, and processing losses of vitamin B6 vary and in some foods may be more the 50% depending on the form of vitamin present in the food. The current Estimated Average Requirements (EARs) for vitamin B6 for women and men ages 14 and up increase with age from 1.0 to 1.3 mg/day and from 1.1 to 1.4 mg/day, respectively; the Recommended Dietary Allowance (RDA) increase with age from 1.2 to 1.5 and from 1.3 to 1.7 mg/day, respectively. It has been reported the B vitamins bolster immune response to fight infection and chronic disease (11).

Garlic (Allium sativum) is one of the oldest medicinal plants used by different cultures (3). The oldest reports of health promoting properties of garlic dated back to $16^{th}$ century BC, when over 20 ailments were purported from Egypt to be efficiently cured by garlic. Garlic stimulates the immune system and acts as a natural antibiotic, not harmful to the friendly bacteria flora. Many laboratory studies have confirmed the antibacterial, antifungal, antivirus, immune-stimulating, and antioxidant properties of garlic. In 1990, the US National Cancer Institute concluded garlic may be a food with cancer-preventive properties.

Echinacea, a member of the Compositae family, is a herb widely used to treat and prevent common illness, as it has been shown to have immune-stimulating properties (3). Three of nine species in this family are of medicinal interest (Echinacea angustifolia, E. pallida and E. purpurea). They are commonly used to treat viral upper respiratory tract infections. Echinacea causes and increase in numbers of circulating white blood cells, activation of phagocytosis by human granulocytes, and elevation of body temperature, resulting from primarily from the aerial portion of E. purpurea and the root portion of E. pallida. Previous research suggest the Echinacea may be most effective at reducing the severity and duration of the common cold when taken early in the illness, but has little to no preventive benefit. A review of five randomized, clinical trials investigating the immunomodulatory activity of Echinacea concluded that Echinacea may be an efficacious immune stimulator. For adults (18 years and older), to stimulate the immune system, five 400 mg doses of Echinacea have been taken by mouth four times daily for 28 days (8). A dose of 8,000 mg of Echinacea has been taken by mouth once daily for 28 days. To treat the common cold in adults, 500-1000 mg of Echinacea three times daily for 5-7 days.

In a review of the evidence supporting complementary and alternative medicine for the treatment and prevention of the common cold in adults(9), it indicated that for prevention, vitamin C demonstrated benefit in patients subjected to cold stress. There is inconsistent evidence for the Asian ginseng (Panax ginseng) and North American ginseng (Panax quinquefolius). Allicin (an organosulfur compounds obtained from garlic) was highly effective in one small trial. For treatment, Echinacea purpurea is most consistently useful variety; it was effective in 5 of 6 trials, likely owing to dose and formulation issues. Overall, the evidence suggests no benefit from probiotics for the prevention or treatment of the common cold.

In another review of the evidence for interventions aimed at preventing and treating the common cold is frequently of poor quality and results are inconsistent (10), it indicated that the best evidence for the prevention of the common cold supports physical interventions (e.g., handwashing) and possibly the use of zinc supplements. The best evidence for non-traditional treatments of the common cold supports the use of oral zinc supplements in adults and honey at bed time for cough in children over one year.

A study from Egypt showed that 62 patients with the common cold were helped by giving them either a natural multiherbal formula containing 120 mg of Echinacea extract, 100 mg of garlic powder, 200 mg of Nigella Sativa oil, and 50 mg of Panax ginseng extract plus vitamin C 50 mg, and element zinc 7.5 mg (Immumax), or placebo treatment for the duration of their symptoms or a maximum of 14 days (3). The researchers found that while the placebo group's average cold duration was eight (5-9) days, the cold duration of the Immumax group was averaging four (3-6) days. Thus, the study showed the use of combination of multiherbal formula plus vitamin C and zinc is helpful in reducing the duration and severity of common cold symptoms.

It has been reported that a composition and a method for stimulating or enhancing the immune system in a human being (2). The composition comprises a mixture of Manapol (a trademark of Carrington Laboratories, Inc., containing acetylated mannans primarily in the form of mannose), beta-1,3-D-glucan, arabinogalactan, elderberry extract, (standardized to about 30% anthocyanins), zinc gluconate and allicin. The composition taken as a food supplement is particularly useful against infectious diseases and acts as an anti-bacterial, anti-viral or anti-fungal agent.

The reports cited above have showed that the ingredients of vitamin C, zinc, vitamin D3, vitamin B6, garlic, and Echinacea, each ingredient alone or in combination with some other materials have been used to stimulate or enhance the immune systems of the human body and to treat the common cold. However, there is no report indicating the use of an alternative composition comprising an effective amount of vitamin C, zinc, vitamin A, vitamin D3, vitamin B6, garlic and Echinacea in the treatment of bacterial or viral infection.

The present invention provides a pharmaceutical composition comprising an effective amount of vitamin, zinc, vitamin D3, vitamin A, vitamin B6, garlic and Echinacea that is able to treat bacterial or viral infection in a patient. In on embodiment, the pharmaceutical composition is a oral composition. In another embodiment the amount of vitamin C is 1100 mg, the amount of zinc is 55 mg, the amount of vitamin A is 50,000 IU, the amount of vitamin D3 is 200 IU, the amount of vitamin B6 is 30 mg, garlic is 35 IU, and Echinacea is 200 mg in the composition, and the composition in tablet form.

The present invention also provides a method for treating bacterial or viral infection in a patient by orally administering a composition to the patient, wherein the composition comprising an amount of vitamin C, zinc, vitamin A, vitamin D3, vitamin B6, garlic and Echinacea effective to reduce the symptoms of bacterial and/or viral infections. In one embodiment, the viral infection is common cold and influenza. In another embodiment, the amount of vitamin C is 1100 mg, D3 is 200 IU, zinc 55 mg., garlic 35 IU, vitamin A 50.000 IU, B6 30 mg, Echinacea 200 mg in the composition, and the composition is in the tablet form. In another embodiment, the method further comprises an intervention such as adding a proper diet containing vegetables, and exercising.

As used herein, "a" or "an" means one or more (or at least one)

As used herein, "patient" means either a human being, either adult or children using the oral composition.

What is claimed is:

1. A pharmaceutical composition comprising an amount of vitamin C, zinc, vitamin A, vitamin D3, vitamin B6, garlic and Echinacea effective to treat bacterial and/or viral infections.

2. The pharmaceutical composition according to claim 1, wherein the composition is an oral composition.

3. The pharmaceutical composition according to claim 1 wherein the amount of vitamin C is 1100 mg, zinc is 55 mg, vitamin A 50,000 IU, vitamin D3 200 IU, vitamin B6 is 30 mg, garlic is 35 IU, and Echinacea is 200 mg, and wherein the composition is in tablet form.

4. The pharmaceutical composition according to claim 1, wherein the viral infections is colds or influenza.

5. A method for treating bacterial and/or viral infections by orally administering a pharmaceutical composition comprising an amount of vitamin C, zinc, vitamin A, vitamin D3, vitamin B6, garlic, and Echinacea to a patient effective to treat bacterial and/or viral infections.

6. The method for treating bacterial and/or viral infections according to claim 5, wherein the amount of vitamin C 1100 mg, zinc 55 mg, vitamin A 50,000 IU, vitamin D3 200 IU, vitamin B6 30 mg, garlic is 35 IU, and Echinacea is 200 mg, and wherein the composition is in tablet form.

7. The method for treating bacterial and/or viral infections according to claim 5, wherein the viral infections is colds or influenza.

8. The method for treating bacterial and/or viral infections according to claim 5, wherein the method further combines with a intervention of using a proper diet containing vegetables and exercising.

* * * * *